United States Patent
Shevgoor

(10) Patent No.: US 9,956,379 B2
(45) Date of Patent: May 1, 2018

(54) CATHETER TUBING WITH EXTRALUMINAL ANTIMICROBIAL COATING

(71) Applicant: Becton, Dickinson and Company, Franklin Lakes, NJ (US)

(72) Inventor: Siddarth K. Shevgoor, Sandy, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days. days.

(21) Appl. No.: 15/596,705

(22) Filed: May 16, 2017

(65) Prior Publication Data
US 2017/0246424 A1    Aug. 31, 2017

Related U.S. Application Data

(62) Division of application No. 14/260,056, filed on Apr. 23, 2014, now Pat. No. 9,675,793.

(51) Int. Cl.
*A61L 29/08* (2006.01)
*A61L 15/46* (2006.01)
(Continued)

(52) U.S. Cl.
CPC ......... *A61M 25/0045* (2013.01); *A61L 29/08* (2013.01); *A61L 29/16* (2013.01);
(Continued)

(58) Field of Classification Search
CPC ......... A61L 29/08; A61L 29/085; A61L 29/16
(Continued)

(56) References Cited

U.S. PATENT DOCUMENTS 3,223,629 A    12/1965  Loeffeler
3,598,127 A *   8/1971  Wepsic ............... A61L 29/16
                                              424/422
(Continued)

FOREIGN PATENT DOCUMENTS

CA    1331333 C    8/1994
CA    2133053 A1   3/1995
(Continued)

OTHER PUBLICATIONS

Anusavice KJ, Zhang N-Z, Shen C. Controlled Release of Chlorhexidine from UDMA-TEGDMA Resin, Journal of dental research, 2006;85(10); 950-954.
(Continued)

*Primary Examiner* — Cachet I Sellman
(74) *Attorney, Agent, or Firm* — Jeanne Lukasave; Craig Metcalf; Kirton McConkie

(57) ABSTRACT

Various methods can be employed to apply an antimicrobial coating to the outer surface of catheter tubing. The antimicrobial coating minimizes the risk of microbe colonization on the outer surface of the catheter tubing when the catheter tubing is positioned within the vasculature of a patient. A catheter can be manufactured using a pre-treatment process which applies the antimicrobial coating to the catheter tubing prior to applying a lubricant over top of the coating. The lubricant can function to retain the coating on the outer surface and also to limit the diffusion of the antimicrobial agent from the coating. A catheter can include an antimicrobial coating that does not block the visibility of flashback. Because the antimicrobial coating can be minimally transparent, the coating can be applied to the outer surface in a striped pattern or other pattern that leaves a portion of the outer surface uncoated or minimally coated. The flashback
(Continued)

will then remain visible through the portions of the catheter tubing where no coating or minimal coating is present.

12 Claims, 13 Drawing Sheets

(51) Int. Cl.
    *A61M 25/00*      (2006.01)
    *A61M 25/01*      (2006.01)
    *A61L 29/16*      (2006.01)
    *A61L 29/18*      (2006.01)
    *B05D 3/12*      (2006.01)
    *B05D 1/18*      (2006.01)

(52) U.S. Cl.
    CPC .......... *A61L 29/18* (2013.01); *A61M 25/0009* (2013.01); *A61M 25/0105* (2013.01); *B05D 1/18* (2013.01); *B05D 3/12* (2013.01); *A61L 2300/404* (2013.01); *A61M 2025/0046* (2013.01)

(58) Field of Classification Search
    USPC .................................. 427/256, 2.28; 604/265
    See application file for complete search history.

(56) References Cited

U.S. PATENT DOCUMENTS

| | | | |
|---|---|---|---|
| 3,695,921 A | 10/1972 | Shepherd | |
| 3,867,937 A | 2/1975 | Schwartz | |
| 3,986,508 A | 10/1976 | Barrington | |
| 4,068,660 A | 1/1978 | Beck | |
| 4,170,996 A | 10/1979 | Wu | |
| 4,280,500 A | 7/1981 | Ono | |
| 4,334,551 A | 6/1982 | Pfister | |
| 4,339,336 A | 7/1982 | Hammond | |
| 4,387,879 A | 6/1983 | Tauschinski | |
| 4,449,693 A | 5/1984 | Gereg | |
| 4,469,483 A * | 9/1984 | Becker ............... | A61M 25/0108 128/DIG. 21 |
| 4,512,766 A | 4/1985 | Vailancourt | |
| 4,584,192 A | 4/1986 | Dell | |
| 4,592,920 A | 6/1986 | Murtfeldt | |
| 4,603,152 A | 7/1986 | Laurin | |
| 4,610,674 A | 9/1986 | Suzuki | |
| 4,629,743 A | 12/1986 | Hong | |
| 4,629,746 A | 12/1986 | Michl | |
| 4,642,126 A | 2/1987 | Zador | |
| 4,676,782 A | 6/1987 | Yamamoto | |
| 4,677,143 A | 6/1987 | Laurin | |
| 4,716,032 A | 12/1987 | Westfall | |
| 4,723,948 A | 2/1988 | Clark | |
| 4,758,225 A | 7/1988 | Cox | |
| 4,781,703 A | 11/1988 | Walker | |
| 4,798,594 A | 1/1989 | Hillstead | |
| 4,838,873 A | 6/1989 | Landskron | |
| 4,842,591 A | 6/1989 | Luther | |
| 4,846,812 A | 7/1989 | Walker | |
| 4,874,377 A | 10/1989 | Newgard | |
| 4,880,414 A | 11/1989 | Whipple | |
| 4,895,566 A | 1/1990 | Lee | |
| 4,897,427 A | 1/1990 | Barnavon | |
| 4,915,934 A | 4/1990 | Tomlinson | |
| 4,917,668 A | 4/1990 | Haindl | |
| 4,925,668 A * | 5/1990 | Khan ....................... | A61L 29/06 264/209.1 |
| 4,933,178 A | 6/1990 | Capelli | |
| 4,935,010 A | 6/1990 | Cox | |
| 4,950,257 A | 8/1990 | Hibbs | |
| 4,955,890 A | 9/1990 | Yamamoto | |
| 4,985,399 A | 1/1991 | Matsuda | |
| 4,990,357 A | 2/1991 | Karakelle | |
| 5,019,096 A | 5/1991 | Fox, Jr. | |
| 5,023,082 A | 6/1991 | Friedman | |
| 5,030,665 A | 7/1991 | Lee | |
| 5,041,097 A | 8/1991 | Johnson | |
| 5,053,014 A | 10/1991 | Van Heugten | |
| 5,062,836 A | 11/1991 | Wendell | |
| 5,064,416 A | 11/1991 | Newgard | |
| 5,077,352 A | 12/1991 | Elton | |
| 5,078,703 A | 1/1992 | Bryant | |
| 5,084,023 A | 1/1992 | Lemieux | |
| 5,085,645 A | 2/1992 | Purdy | |
| 5,098,410 A | 3/1992 | Kerby | |
| 5,108,374 A | 4/1992 | Lemieux | |
| 5,127,905 A | 7/1992 | Lemieux | |
| 5,154,703 A | 10/1992 | Bonaldo | |
| 5,156,596 A | 10/1992 | Balbierz | |
| 5,167,647 A | 12/1992 | Wijkamp | |
| 5,217,493 A | 6/1993 | Raad | |
| 5,226,898 A | 7/1993 | Gross | |
| 5,234,410 A | 8/1993 | Graham | |
| 5,242,425 A | 9/1993 | White | |
| 5,256,145 A | 10/1993 | Atkinson | |
| 5,290,246 A | 3/1994 | Yamamoto | |
| 5,295,969 A | 3/1994 | Fischell | |
| 5,330,435 A | 7/1994 | Vaillancourt | |
| 5,330,449 A | 7/1994 | Prichard | |
| 5,350,363 A | 9/1994 | Goode | |
| 5,352,205 A | 10/1994 | Dales | |
| 5,357,636 A | 10/1994 | Dresdner, Jr. | |
| 5,366,505 A | 11/1994 | Farber | |
| 5,380,301 A | 1/1995 | Prichard | |
| 5,405,323 A | 4/1995 | Rogers | |
| 5,405,338 A | 4/1995 | Kranys | |
| 5,456,675 A | 10/1995 | Wolbring | |
| 5,456,948 A | 10/1995 | Mathisen | |
| 5,487,728 A | 1/1996 | Vaillancourt | |
| 5,512,199 A | 4/1996 | Khan | |
| 5,520,666 A | 5/1996 | Choudhury | |
| 5,536,258 A | 7/1996 | Folden | |
| 5,540,661 A | 7/1996 | Tomisaka | |
| 5,547,662 A | 8/1996 | Khan | |
| 5,549,566 A | 8/1996 | Elias | |
| 5,549,577 A | 8/1996 | Siegel | |
| 5,575,769 A | 11/1996 | Vaillancourt | |
| 5,589,120 A * | 12/1996 | Khan .................... | A61L 29/085 264/130 |
| 5,613,663 A | 3/1997 | Schmidt | |
| 5,616,338 A | 4/1997 | Fox, Jr. | |
| 5,620,434 A | 4/1997 | Brony | |
| 5,629,006 A | 5/1997 | Hoang | |
| 5,638,812 A | 6/1997 | Turner | |
| 5,651,772 A | 7/1997 | Arnett | |
| 5,653,695 A | 8/1997 | Hopkins | |
| 5,657,963 A | 8/1997 | Hinchliffe | |
| 5,658,253 A | 8/1997 | Piontek | |
| 5,688,747 A | 11/1997 | Khan | |
| 5,697,915 A | 12/1997 | Lynn | |
| 5,698,229 A | 12/1997 | Ohsumi | |
| 5,712,229 A | 1/1998 | Hopkins | |
| 5,716,406 A | 2/1998 | Farber | |
| 5,738,144 A | 4/1998 | Rogers | |
| 5,749,861 A | 5/1998 | Guala | |
| 5,763,412 A | 6/1998 | Khan | |
| 5,773,487 A | 6/1998 | Sokol | |
| 5,806,831 A | 9/1998 | Paradis | |
| 5,810,768 A | 9/1998 | Lopez | |
| 5,817,069 A | 10/1998 | Arnett | |
| 5,827,239 A | 10/1998 | Dillon | |
| 5,830,196 A | 11/1998 | Hicks | |
| 5,830,401 A | 11/1998 | Prichard | |
| 5,833,674 A | 11/1998 | Turnbull | |
| 5,843,046 A | 12/1998 | Motisi | |
| 5,861,440 A | 1/1999 | Gohla | |
| 5,911,710 A | 6/1999 | Barry | |
| 5,944,712 A * | 8/1999 | Frassica ................ | A61M 25/00 600/434 |
| 5,951,519 A | 9/1999 | Utterberg | |
| 5,954,698 A | 9/1999 | Pike | |
| 5,957,898 A | 9/1999 | Jepson | |
| 5,967,490 A | 10/1999 | Pike | |
| 6,039,302 A | 3/2000 | Cote, Sr. | |

(56) References Cited

U.S. PATENT DOCUMENTS

| | | |
|---|---|---|
| 6,046,143 A | 4/2000 | Khan |
| 6,051,609 A | 4/2000 | Yu |
| 6,068,622 A | 5/2000 | Sater |
| 6,074,379 A | 6/2000 | Prichard |
| 6,077,244 A | 6/2000 | Botich |
| 6,102,890 A | 8/2000 | Stivland |
| 6,117,108 A | 9/2000 | Woehr |
| 6,120,784 A | 9/2000 | Snyder, Jr. |
| 6,127,320 A | 10/2000 | Van Ooij |
| 6,156,054 A | 12/2000 | Zadno-Azizi |
| 6,165,168 A | 12/2000 | Russo |
| 6,171,287 B1 | 1/2001 | Lynn |
| 6,217,566 B1 | 4/2001 | Ju |
| 6,228,073 B1 | 5/2001 | Noone |
| 6,242,526 B1 | 6/2001 | Siddiqui |
| 6,245,098 B1 | 6/2001 | Feeser |
| 6,248,811 B1 | 6/2001 | Ottersbach |
| 6,273,404 B1 | 8/2001 | Holman |
| 6,273,869 B1 | 8/2001 | Vaillancourt |
| 6,326,417 B1 | 12/2001 | Jia |
| 6,332,874 B1 | 12/2001 | Eliasen |
| 6,337,357 B1 | 1/2002 | Fukunishi |
| 6,344,218 B1 | 2/2002 | Dodd |
| 6,353,041 B1 | 3/2002 | Qian |
| 6,387,075 B1 | 5/2002 | Stivland |
| 6,413,539 B1 | 7/2002 | Shalaby |
| 6,426,373 B1 | 7/2002 | Stange |
| 6,475,434 B1 | 11/2002 | Darouiche |
| 6,485,473 B1 | 11/2002 | Lynn |
| 6,488,942 B1 | 12/2002 | Ingemann |
| 6,492,445 B2 | 12/2002 | Siddiqui |
| 6,503,353 B1 | 1/2003 | Peterson |
| 6,511,462 B1 | 1/2003 | Itou |
| 6,544,214 B1 | 4/2003 | Utterberg |
| 6,575,958 B1 | 6/2003 | Happ |
| 6,575,960 B2 | 6/2003 | Becker |
| 6,576,633 B1 | 6/2003 | Young |
| 6,579,221 B1 | 6/2003 | Peterson |
| 6,579,539 B2 | 6/2003 | Lawson |
| 6,595,981 B2 | 7/2003 | Huet |
| 6,663,614 B1 | 12/2003 | Carter |
| 6,699,221 B2 | 3/2004 | Vaillancourt |
| 6,719,726 B2 | 4/2004 | Meng |
| 6,719,991 B2 | 4/2004 | Darouiche |
| 6,723,350 B2 | 4/2004 | Burrell |
| 6,740,063 B2 | 5/2004 | Lynn |
| 6,808,161 B1 | 10/2004 | Hishikawa |
| 6,843,784 B2 | 1/2005 | Modak |
| 6,846,846 B2 | 1/2005 | Modak |
| 6,861,060 B1 | 3/2005 | Luriya |
| 6,883,778 B1 | 4/2005 | Newton |
| 6,887,270 B2 | 5/2005 | Miller |
| 6,893,456 B2 | 5/2005 | Lumauig |
| 6,896,889 B2 | 5/2005 | Chevalier |
| 7,008,404 B2 | 3/2006 | Nakajima |
| 7,074,839 B2 | 7/2006 | Fansler |
| 7,098,256 B2 | 8/2006 | Ong |
| 7,115,183 B2 | 10/2006 | Larson |
| 7,179,849 B2 | 2/2007 | Terry |
| 7,198,800 B1 | 4/2007 | Ko |
| 7,232,428 B1 | 6/2007 | Inukai |
| 7,232,540 B2 | 6/2007 | Gould |
| 7,261,925 B2 | 8/2007 | Nesbitt |
| 7,268,165 B2 | 9/2007 | Greten |
| 7,347,839 B2 | 3/2008 | Hiejima |
| 7,374,798 B2 | 5/2008 | Choo |
| 7,396,346 B2 | 7/2008 | Nakajima |
| 7,407,707 B2 | 8/2008 | Gould |
| 7,462,401 B2 | 12/2008 | Halfyard |
| 7,470,254 B2 | 12/2008 | Basta |
| 7,494,339 B2 | 2/2009 | Dias |
| 7,498,367 B2 | 3/2009 | Qian |
| 7,514,477 B2 | 4/2009 | Klare |
| 7,608,082 B2 | 10/2009 | Cuevas |
| 7,704,935 B1 | 4/2010 | Davis |
| 7,736,339 B2 | 6/2010 | Woehr |
| 7,816,434 B2 | 10/2010 | Hackbarth |
| 7,871,649 B2 | 1/2011 | Modak |
| 7,874,467 B2 | 1/2011 | Pardes |
| 7,914,494 B2 | 3/2011 | Hiejima |
| 7,981,475 B2 | 7/2011 | Takahashi |
| 8,034,454 B2 | 10/2011 | Terry |
| 8,034,455 B2 | 10/2011 | Wang |
| 8,067,402 B2 | 11/2011 | Whiteford |
| 8,133,423 B2 | 3/2012 | Tang |
| 8,227,050 B1 | 7/2012 | O'Neil |
| 8,231,602 B2 | 7/2012 | Anderson |
| 8,263,102 B2 | 9/2012 | Labrecque |
| 8,268,381 B2 | 9/2012 | Whiteford |
| 8,343,523 B2 | 1/2013 | Toreki |
| 8,343,525 B2 | 1/2013 | Davis |
| 8,353,876 B2 | 1/2013 | Suwito |
| 8,357,119 B2 | 1/2013 | Stout |
| 8,388,583 B2 | 3/2013 | Stout |
| 8,414,547 B2 | 4/2013 | Difiore |
| 8,512,294 B2 | 8/2013 | Ou-Yang et al. |
| 8,574,171 B2 * | 11/2013 | Nesbitt .................. A61L 31/10 427/2.1 |
| 8,622,995 B2 | 1/2014 | Ziebol |
| 8,622,996 B2 | 1/2014 | Ziebol |
| 8,691,887 B2 | 4/2014 | Ou-Yang |
| 8,728,030 B2 | 5/2014 | Woehr |
| 8,840,927 B2 | 9/2014 | Ditizio |
| 9,078,441 B2 | 7/2015 | Raad |
| 9,138,252 B2 | 9/2015 | Bierman |
| 2001/0010016 A1 | 7/2001 | Modak |
| 2001/0016589 A1 | 8/2001 | Modak |
| 2001/0018095 A1 | 8/2001 | Shlenker |
| 2001/0032006 A1 | 10/2001 | Griffin |
| 2001/0049519 A1 | 12/2001 | Holman |
| 2001/0053895 A1 | 12/2001 | Vaillancourt |
| 2001/0056133 A1 | 12/2001 | Montgomery |
| 2002/0009436 A1 | 1/2002 | Doyle |
| 2002/0022660 A1 | 2/2002 | Jampani |
| 2002/0028751 A1 | 3/2002 | Lokkesmoe |
| 2002/0037260 A1 | 3/2002 | Budny |
| 2002/0040092 A1 | 4/2002 | Siddiqui |
| 2002/0064858 A1 | 5/2002 | Yacoby-Zeevi |
| 2002/0091424 A1 | 7/2002 | Biel |
| 2002/0119111 A1 | 8/2002 | Kilgour |
| 2002/0133124 A1 | 9/2002 | Leinsing |
| 2002/0144705 A1 | 10/2002 | Brattesani |
| 2003/0023208 A1 | 1/2003 | Osypka |
| 2003/0060804 A1 | 3/2003 | Vaillancourt |
| 2003/0068667 A1 | 4/2003 | Olson |
| 2003/0072781 A1 | 4/2003 | Pelerin |
| 2003/0105143 A1 | 6/2003 | Ammendola |
| 2003/0119932 A1 | 6/2003 | Al-Akhdar |
| 2003/0134783 A1 | 7/2003 | Harshey |
| 2003/0144362 A1 | 7/2003 | Utterberg |
| 2003/0147932 A1 | 8/2003 | Nun |
| 2003/0162839 A1 | 8/2003 | Symington |
| 2003/0170308 A1 | 9/2003 | Cleary |
| 2003/0176848 A1 | 9/2003 | Gibson |
| 2003/0206875 A1 | 11/2003 | Budny |
| 2003/0215433 A1 | 11/2003 | Kokai-Kun |
| 2003/0224032 A1 | 12/2003 | Read |
| 2004/0013574 A1 | 1/2004 | Conway |
| 2004/0013703 A1 | 1/2004 | Ralph |
| 2004/0014864 A1 | 1/2004 | Milic |
| 2004/0039349 A1 | 2/2004 | Modak |
| 2004/0058829 A1 | 3/2004 | Hei |
| 2004/0062592 A1 * | 4/2004 | Shekalim ................ A61L 31/10 401/208 |
| 2004/0109852 A1 | 6/2004 | Xu |
| 2004/0115477 A1 | 6/2004 | Nesbitt |
| 2004/0132164 A1 | 7/2004 | Doyle |
| 2004/0180829 A1 | 9/2004 | Bassler |
| 2004/0185296 A1 | 9/2004 | Mazzanti |
| 2004/0230162 A1 | 11/2004 | Tan |
| 2004/0234475 A1 | 11/2004 | Lannibois-Drean |
| 2005/0008671 A1 | 1/2005 | Van Antwerp |
| 2005/0048005 A1 | 3/2005 | Stockel |
| 2005/0048124 A1 | 3/2005 | Sarangapani |

(56) References Cited

U.S. PATENT DOCUMENTS

| | | |
|---|---|---|
| 2005/0059731 A1 | 3/2005 | Albrecht |
| 2005/0080158 A1 | 4/2005 | Ong |
| 2005/0100580 A1 | 5/2005 | Osborne |
| 2005/0118239 A1 | 6/2005 | Sabesan |
| 2005/0124970 A1 | 6/2005 | Kunin |
| 2005/0131356 A1 | 6/2005 | Ash |
| 2005/0143286 A1 | 6/2005 | Singh |
| 2005/0148928 A1 | 7/2005 | Molina |
| 2005/0158253 A1 | 7/2005 | Budny |
| 2005/0176905 A1 | 8/2005 | Moon |
| 2005/0209581 A1 | 9/2005 | Butts |
| 2005/0209583 A1 | 9/2005 | Powers |
| 2005/0233950 A1 | 10/2005 | Madhyastha |
| 2005/0265931 A1 | 12/2005 | Qian |
| 2006/0024372 A1 | 2/2006 | Utterberg |
| 2006/0051385 A1 | 3/2006 | Scholz |
| 2006/0064159 A1 | 3/2006 | Porter |
| 2006/0163515 A1 | 7/2006 | Ruschke |
| 2006/0165751 A1 | 7/2006 | Chudzik |
| 2006/0165903 A1 | 7/2006 | Mazzanti |
| 2006/0177477 A1 | 8/2006 | Ash |
| 2006/0239954 A1 | 10/2006 | Sancho |
| 2006/0258780 A1 | 11/2006 | Chaussade |
| 2006/0259012 A1 | 11/2006 | Propp |
| 2006/0281663 A1 | 12/2006 | Asmus |
| 2007/0000407 A1 | 1/2007 | Leong |
| 2007/0083157 A1 | 4/2007 | Belley |
| 2007/0083162 A1 | 4/2007 | O'Reagan |
| 2007/0112112 A1 | 5/2007 | Kerschner |
| 2007/0112146 A1 | 5/2007 | Falk |
| 2007/0129690 A1* | 6/2007 | Rosenblatt .............. A61L 29/16 604/265 |
| 2007/0141524 A1 | 6/2007 | Brennan |
| 2007/0160547 A1 | 7/2007 | Duffy |
| 2007/0166344 A1 | 7/2007 | Qu |
| 2007/0202177 A1 | 8/2007 | Hoang |
| 2007/0203574 A1 | 8/2007 | McGrath |
| 2007/0225179 A1 | 9/2007 | Schutz |
| 2007/0233007 A1 | 10/2007 | Adams |
| 2007/0275101 A1 | 11/2007 | Lu |
| 2007/0281198 A1 | 12/2007 | Lousenberg |
| 2008/0026026 A1 | 1/2008 | Lu |
| 2008/0027410 A1 | 1/2008 | Harding |
| 2008/0039796 A1 | 2/2008 | Nakajima |
| 2008/0051737 A1 | 2/2008 | Paul |
| 2008/0075761 A1 | 3/2008 | Modak |
| 2008/0103487 A1 | 5/2008 | Miyasaka |
| 2008/0108944 A1 | 5/2008 | Woehr |
| 2008/0119789 A1 | 5/2008 | Kaemmerer |
| 2008/0161763 A1 | 7/2008 | Harding |
| 2008/0182921 A1 | 7/2008 | Suh |
| 2008/0194707 A1 | 8/2008 | Potter |
| 2009/0012220 A1 | 1/2009 | Yamane |
| 2009/0036768 A1 | 2/2009 | Seehusen |
| 2009/0062766 A1 | 3/2009 | Howlett |
| 2009/0101152 A1 | 4/2009 | Burk |
| 2009/0110844 A1 | 4/2009 | Platzer |
| 2009/0114327 A1 | 5/2009 | Breunig |
| 2009/0117164 A1 | 5/2009 | Toreki |
| 2009/0125118 A1 | 5/2009 | Gong |
| 2009/0157007 A1 | 6/2009 | McKinnon |
| 2009/0162530 A1* | 6/2009 | Nesbitt .................. A61L 29/106 427/2.3 |
| 2009/0176907 A1 | 7/2009 | Subramanian |
| 2009/0188559 A1 | 7/2009 | Nesbitt |
| 2009/0211909 A1* | 8/2009 | Nesbitt .................. A61L 31/10 204/487 |
| 2009/0220739 A1 | 9/2009 | Chougule |
| 2009/0226541 A1 | 9/2009 | Scholz |
| 2009/0281525 A1 | 11/2009 | Harding |
| 2009/0299452 A1* | 12/2009 | Eidenschink .............. A61F 2/95 623/1.11 |
| 2009/0317435 A1 | 12/2009 | Vandesteeg |
| 2009/0324666 A1 | 12/2009 | Krongauz |
| 2010/0015200 A1 | 1/2010 | McClain |
| 2010/0024648 A1 | 2/2010 | Breault |
| 2010/0069854 A1 | 3/2010 | Okoh |
| 2010/0106102 A1 | 4/2010 | Ziebol |
| 2010/0106103 A1 | 4/2010 | Ziebol |
| 2010/0135949 A1 | 6/2010 | Ou-Yang |
| 2010/0136209 A1 | 6/2010 | Ou-Yang |
| 2010/0137379 A1 | 6/2010 | Ou-Yang |
| 2010/0137472 A1 | 6/2010 | Ou-Yang |
| 2010/0200017 A1 | 8/2010 | Kerr |
| 2010/0204648 A1 | 8/2010 | Stout |
| 2010/0204675 A1 | 8/2010 | Woehr |
| 2010/0222746 A1 | 9/2010 | Burkholz |
| 2011/0009831 A1* | 1/2011 | Burkholz .............. A61L 29/085 604/265 |
| 2011/0065798 A1 | 3/2011 | Hoang |
| 2011/0146680 A1 | 6/2011 | Conway |
| 2011/0150958 A1 | 6/2011 | Davis |
| 2011/0160662 A1 | 6/2011 | Stout |
| 2011/0160663 A1 | 6/2011 | Stout |
| 2011/0218529 A1 | 9/2011 | Garcia |
| 2011/0301553 A1* | 12/2011 | Goral .................... A01N 25/04 604/265 |
| 2011/0319825 A1 | 12/2011 | Goral |
| 2012/0016318 A1 | 1/2012 | Hoang et al. |
| 2012/0078203 A1 | 3/2012 | Gaube |
| 2012/0083750 A1 | 4/2012 | Sansoucy |
| 2012/0103448 A1 | 5/2012 | Hopf |
| 2012/0111368 A1 | 5/2012 | Rahimy et al. |
| 2013/0090607 A1 | 4/2013 | McKinnon |
| 2013/0165868 A1 | 6/2013 | Isaacson |
| 2013/0196079 A1 | 8/2013 | Schwalm |
| 2013/0197485 A1 | 8/2013 | Gardner et al. |
| 2013/0204231 A1 | 8/2013 | Ziebol et al. |
| 2013/0245568 A1 | 9/2013 | Kerr |
| 2013/0274686 A1 | 10/2013 | Ziebol |
| 2013/0310764 A1 | 11/2013 | Burkholz |
| 2013/0330387 A1 | 12/2013 | Ou-yang |
| 2016/0008517 A1 | 1/2016 | Burkholz |
| 2017/0095596 A1 | 4/2017 | Petrak et al. |

FOREIGN PATENT DOCUMENTS

| | | |
|---|---|---|
| CN | 1187598 | 7/1998 |
| CN | 1526771 C | 9/2004 |
| CN | 101353545 B | 1/2009 |
| CN | 102070983 A | 5/2011 |
| DE | 3913392 C2 | 10/1990 |
| DE | 202009009602 U1 | 12/2009 |
| EP | 0036294 A2 | 9/1981 |
| EP | 0070087 B1 | 1/1983 |
| EP | 0227230 A1 | 7/1987 |
| EP | 0338418 B1 | 10/1989 |
| EP | 0370997 A2 | 5/1990 |
| EP | 0379271 B1 | 7/1990 |
| EP | 0396431 B1 | 11/1990 |
| EP | 0414997 B1 | 3/1991 |
| EP | 0778337 A2 | 6/1997 |
| EP | 0992252 B1 | 4/2000 |
| EP | 1466645 B1 | 10/2004 |
| EP | 1679043 B1 | 7/2006 |
| JP | 05277434 B2 | 10/1993 |
| JP | 0747435 | 2/1995 |
| JP | H08209064 A | 8/1996 |
| JP | H08311373 A | 11/1996 |
| JP | 09151262 A | 6/1997 |
| JP | H09157548 A | 6/1997 |
| JP | H09176677 B2 | 7/1997 |
| JP | 09-324135 | 12/1997 |
| JP | 10231 | 1/1998 |
| JP | H11322560 B2 | 11/1999 |
| JP | 2000178475 A | 6/2000 |
| JP | 2000264803 B2 | 9/2000 |
| JP | 2001072438 A | 3/2001 |
| JP | 2002282762 B2 | 10/2002 |
| JP | 2003342402 A | 12/2003 |
| JP | 2004043669 A | 2/2004 |
| JP | 2005028209 A | 2/2005 |
| JP | 2005515838 A | 6/2005 |
| JP | 2005520912 A | 7/2005 |

(56) References Cited

FOREIGN PATENT DOCUMENTS

| | | |
|---|---|---|
| JP | 2007016096 A | 1/2007 |
| JP | WO 2008-533051 | 8/2008 |
| JP | 2009-544454 | 12/2009 |
| JP | 2010-174075 | 8/2010 |
| JP | 2010536836 B2 | 12/2010 |
| JP | 2012-510559 | 5/2012 |
| JP | 2012532681 B2 | 12/2012 |
| KR | 20020066429 B1 | 8/2002 |
| KR | 20080039460 A | 5/2008 |
| WO | WO 9422522 A1 | 10/1994 |
| WO | WO 9521648 A1 | 8/1995 |
| WO | WO 9616690 A1 | 6/1996 |
| WO | WO 9640359 A1 | 12/1996 |
| WO | WO 9858690 A1 | 12/1998 |
| WO | WO 9858989 A1 | 12/1998 |
| WO | WO 9916498 A1 | 4/1999 |
| WO | WO 9932168 A1 | 7/1999 |
| WO | WO 9934849 A1 | 7/1999 |
| WO | WO 9936490 A1 | 7/1999 |
| WO | WO 9943971 A1 | 9/1999 |
| WO | WO 0066189 A2 | 11/2000 |
| WO | WO 0074743 A1 | 12/2000 |
| WO | WO 0195862 A1 | 12/2001 |
| WO | WO 2004071568 A1 | 8/2004 |
| WO | WO 2004108091 A2 | 12/2004 |
| WO | WO 2005037340 A2 | 4/2005 |
| WO | WO 2006012446 A2 | 2/2006 |
| WO | WO 2006056482 A1 | 6/2006 |
| WO | WO 2006074666 A2 | 7/2006 |
| WO | WO 2006088288 A1 | 8/2006 |
| WO | WO 2006099358 A2 | 9/2006 |
| WO | WO 2006099359 A2 | 9/2006 |
| WO | WO 2006100442 A1 | 9/2006 |
| WO | WO 2007064835 A2 | 6/2007 |
| WO | WO 2007095576 A2 | 8/2007 |
| WO | WO 2007100653 A2 | 9/2007 |
| WO | WO 2007100776 A2 | 9/2007 |
| WO | WO 2008014438 A2 | 1/2008 |
| WO | WO 2008014447 A2 | 1/2008 |
| WO | WO 2008031601 A1 | 3/2008 |
| WO | WO 2008045761 A2 | 4/2008 |
| WO | WO 2008052790 A2 | 5/2008 |
| WO | WO 2008128896 A2 | 10/2008 |
| WO | WO 2008132045 A2 | 11/2008 |
| WO | WO 2009012336 A1 | 1/2009 |
| WO | WO 2009070227 A1 | 6/2009 |
| WO | WO 2009114833 A1 | 9/2009 |
| WO | 2010/034470 | 4/2010 |
| WO | WO 2010093791 A1 | 8/2010 |
| WO | WO 2011005951 A2 | 1/2011 |
| WO | WO 2011034675 A2 | 3/2011 |
| WO | WO 2011048204 A2 | 4/2011 |
| WO | WO 2011118680 | 9/2011 |
| WO | WO 2012036916 A1 | 3/2012 |
| WO | WO 2013009998 A2 | 1/2013 |
| WO | WO 2013134421 A1 | 9/2013 |

OTHER PUBLICATIONS

Cabot Corporation, "Using Silicas and Aluminas in Coatins," www.cabot-corp.com/Silicas-And-Aluminas/Coatings, downloaded from the internet on Apr. 26, 2011.

Ciba Irgacure 500 data sheet from Ciba Specialty Chemicals, online, retrieved on [Dec. 13, 2015]. Retrieved from internet see below.

ComfortCoat Hydrophilic Coating, DSM in Medical, http://www.dsm.com/en_US/medical/public/home/pages/product-coating-comfortcoat.jsp, Updated Jan. 11, 2013 Printed Apr. 22, 2013.

Elson Silva, PhD, "Respecting Hydrology Science in the Patenting System," pp. 1-7, Jan. 13, 2011.

Enluria, ChloraPrep, http://enluria.com/products/cloraPrep-product.html, pp. 1-3, Oct. 21, 2008.

Gama Healthcare, Clinell Alcoholic 2% Chlorhexidine, http//www.gamahealthcare.com/clinellaca2c.html, pp. 1-3, Nov. 7, 2008.

Gerald McDonnell and A. Denver Russell, Antiseptics and Disinfectants: Activity, Action and Resistance, Clinical Microbiology Reviews, vol. 12, Jan. 1999, p. 147-179.

Lubricant—Lubricious Hydrophillic Coatings for Medical Devices, Harland Medical Systems, http://www.harlandmedical.com/index.php/materials/lubricent.html, pp. 1-2, Printed Apr. 22, 2013.

Sage Products, Inc., Address Multi-Drug Reistant Organism on the Skin with Early Preop Prep, http://www.sageproducts.com/products/ssi-prevention.cfm, 1 page, Oct. 31, 2008.

Sage Products, Inc., Preoperative Skin Preparation and Preoperative Oral Care for the Short-Term Ventilated Patient, http://www.sageproducts.com/products/ssi-can-prevention.cfm 1 page, Oct. 31, 2008.

Sage Products, Inc., Preoperative Skin Preparation for the Surgical Patient, http://www.sageproducts.com/products/skin-prep.cfm, 1 page, Oct. 31, 2008.

UV & EB Cure, Xiper Innovations, Inc., http://xiperinnovations.com/uv_eb_cure, Printed Apr. 22, 2013.

Ciba IRGACURE 500 data sheet from Ciba Specialty Chemicals online, retrieved on Dec. 13, 2015. http://www.conguimica.com/wp-content/uploads/2015/06/ft_irgacure_500.pdf.

Sage Products, Inc., Preoperative Skin Preparation and Preoperative Oral Care for the Short-Term Ventilated Patient, http://www.sageproducts.com/products/ssi-can-prevention.cfm, p. 1, Oct. 31, 2008.

* cited by examiner

CATHETER TUBING WITH EXTRALUMINAL ANTIMICROBIAL COATING

RELATED APPLICATIONS

This application is a divisional of U.S. patent application Ser. No. 14/260,056, filed Apr. 23, 2014, titled CATHETER TUBING WITH EXTRALUMINAL ANTIMICROBIAL COATING, and is incorporated herein by reference.

BACKGROUND OF THE INVENTION

The present invention relates generally to catheters having an antimicrobial coating on an outside surface of the catheter tubing and to methods for manufacturing such catheters.

Peripherally inserted central catheters and other central venous catheters have been associated with increased rates of nosocomial infection. Typically, nosocomial infections resulting from catheters are due to biofilm formation along the outer surface of the catheter tubing. To address this issue, many central venous catheters are manufactured with an antimicrobial coating on the outer surfaces of the catheter tubing. Such coatings minimize the possibility that microbes will colonize on the surface while the catheter tubing is positioned within the vasculature of the patient.

Peripheral intravenous catheters typically have shorter dwell times than central venous catheters which inherently reduces the risk of biofilm formation on the outer surfaces of peripheral intravenous catheters. In spite of this, there is still a risk of nosocomial infection due to biofilm formation on the outer surfaces of peripheral intravenous catheters.

Although the current techniques used for applying antimicrobial coatings to the outer surface of catheter tubing are effective for central venous catheters, these techniques are oftentimes inadequate for peripheral intravenous catheters. For example, peripheral intravenous catheters are oftentimes configured to allow blood flashback to be visible during insertion of the catheter. The coatings typically used on central venous catheters, however, have poor transparency and therefore block the visibility of the flashback. Also, during manufacture of peripheral intravenous catheters, it is common to stretch the tubing during flaring or swaging processes. When catheter tubing that has been treated using current antimicrobial coatings is stretched, the coating oftentimes tears rendering the catheter unusable. Accordingly, current techniques for applying an antimicrobial coating to catheter tubing have proven to be inadequate for use on peripheral intravenous catheters.

BRIEF SUMMARY OF THE INVENTION

The present invention extends to catheters that include an antimicrobial coating on an outer surface of the catheter tubing and to methods for manufacturing catheters with such coatings. The antimicrobial coating minimizes the risk of microbe colonization on the outer surface of the catheter tubing when the catheter tubing is positioned within the vasculature of a patient.

In some embodiments, a catheter can be manufactured using a pre-treatment process which applies the antimicrobial coating to the catheter tubing prior to applying a lubricant over top of the coating. In such cases, the lubricant can function to retain the coating on the outer surface and also to limit the diffusion of the antimicrobial agent from the coating.

In some embodiments, a catheter can include an antimicrobial coating that does not block the visibility of flashback. Because the antimicrobial coating can be minimally transparent, the coating can be applied to the outer surface in a striped pattern or other pattern that leaves a portion of the outer surface uncoated or minimally coated. The flashback will then remain visible through the portions of the catheter tubing where no coating or minimal coating is present.

In one exemplary embodiment, the present invention is implemented as method for applying an antimicrobial coating on catheter tubing. A solution containing a solvent and an antimicrobial agent can be applied to a surface of catheter tubing. The solvent is then allowed to evaporate to leave behind a coating of the antimicrobial agent on the surface of the catheter tubing. A lubricant is then applied overtop the coating. The lubricant limits the rate of diffusion of the antimicrobial agent from the coating once the surface of the catheter tubing is subject to a fluid.

In some embodiments, the solvent has a vapor pressure that is at least equal to atmospheric pressure at a first temperature with the first temperature being the maximum safe temperature of the antimicrobial agent.

In some embodiments, the solvent comprises ethanol and the antimicrobial agent comprises chlorhexidine gluconate.

In some embodiments, the solvent causes the catheter tubing to expand to allow the antimicrobial agent to penetrate into the catheter tubing.

In another exemplary embodiment, the present invention is implemented as a method for applying an antimicrobial coating to catheter tubing in a pattern. An antimicrobial coating is applied over an outer surface of catheter tubing. The catheter tubing is then passed through a die to remove a portion of the antimicrobial coating from the outer surface such that a pattern of antimicrobial coating remains on the outer surface after the catheter tubing has passed through the die.

In some embodiments, the pattern comprises one or more stripes of antimicrobial coating.

In some embodiments, the outer surface of the catheter tubing comprises one or more channels and the pattern comprises the antimicrobial coating within the one or more channels.

In some embodiments, the pattern comprises one or more portions of the outer surface that do not include the antimicrobial coating or that include an insignificant amount of the antimicrobial coating so that contents of a lumen of the catheter tubing remain visible through the one or more portions.

In some embodiments, the pattern conforms to radiopaque material contained within the catheter tubing.

In some embodiments, the die includes one or more channels on an inner surface of the die. The one or more channels form the pattern.

In some embodiments, the catheter tubing comprises a segment of catheter tubing having a tip, and the antimicrobial coating is not applied to the tip.

In some embodiments, prior to applying the antimicrobial coating to the outer surface of the catheter tubing, a mandrel is inserted into one end of the catheter tubing to prevent the antimicrobial coating from entering the end. In some embodiments, this end comprises an end opposite a tip formed on the catheter tubing.

In another exemplary embodiment, the present invention is implemented as catheter tubing that comprises an outer surface having a circumference; and an antimicrobial coating applied to the outer surface in a pattern such that the pattern does not cover the entire circumference of the outer surface.

In some embodiments, the pattern comprises a plurality of stripes that are formed on the outer surface by passing the catheter tubing through a die after the antimicrobial coating is applied over the entire circumference of the outer surface.

In some embodiments, the plurality of stripes are formed within a plurality of channels in the outer surface.

In some embodiments, the catheter tubing further comprises strips of radiopaque material that extend along a length of the catheter tubing. The plurality of stripes of the pattern run substantially parallel with the strips of radiopaque material.

In some embodiments, the catheter tubing comprises a tip to which the antimicrobial coating does not extend.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1A illustrates catheter tubing 100 prior to the application of an antimicrobial coating. FIG. 1B illustrates catheter tubing 100 after the application of an antimicrobial coating 101. FIG. 1C illustrates catheter tubing 100 after the application of a lubricant 102 overtop of antimicrobial coating 101.

FIG. 2A illustrates catheter tubing 100 being dipped into a solution 200 that includes an evaporating solvent and an antimicrobial agent. FIG. 2B illustrates catheter tubing 100 after being removed from solution 200 with the evaporating solvent evaporating while leaving the antimicrobial agent on the outer surface of catheter tubing 100. FIG. 2C illustrates antimicrobial coating 101 that remains on catheter tubing 100 after the evaporating solvent has evaporated. FIG. 2D illustrates a lubricant 102 that has been applied to catheter tubing 100 overtop of antimicrobial coating 101.

FIG. 3A illustrates a perspective view of catheter tubing 300 with strips of radiopaque material 305 running lengthwise within the catheter tubing. FIG. 3B illustrates a cross-sectional view of catheter tubing 300. FIG. 3C illustrates catheter tubing 300 once antimicrobial coating 301 is applied to the exterior surfaces of the catheter tubing overtop the strips of radiopaque material 305.

FIG. 4A illustrates a perspective view of catheter tubing 400 with strips of radiopaque material 405 running lengthwise within the catheter tubing. FIG. 4B illustrates a cross-sectional view of catheter tubing 400 showing how channels 406 generally align with the strips of radiopaque material 405. FIG. 4C illustrates catheter tubing 400 once antimicrobial coating 301 is applied within channels 406.

FIG. 5A illustrates a top view of an example die 580 having six channels 501 formed on the inner surface of the die for forming a six-striped pattern. FIG. 5B illustrates a cross-sectional view of catheter tubing 300 as it passes through die 580 thereby leaving six stripes of antimicrobial coating 301. FIG. 5C illustrates how catheter tubing 300 can be passed through die 580 after the catheter tubing has been dipped in a solution containing antimicrobial coating 301.

FIG. 6A illustrates an example of a catheter tubing 600 where the antimicrobial coating 301 has been applied to the body of the catheter tubing but not to the tip. FIG. 6B illustrates how the antimicrobial coating 301 can be applied to catheter tubing 600 without applying the coating to the tip while using a dye 680 to apply the coating in a pattern.

DETAILED DESCRIPTION OF THE INVENTION

Figure 1A:
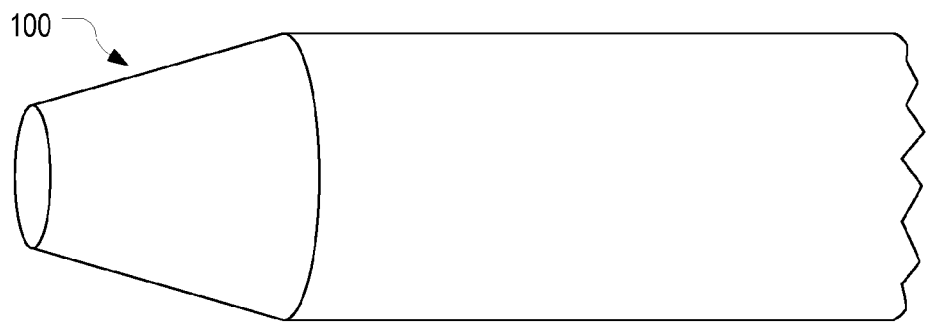
FIGS. 1A-1C illustrate a portion of a catheter tubing 100 during various stages of manufacturer.

The present invention extends to catheters that include an antimicrobial coating on an outer surface of the catheter tubing and to methods for manufacturing catheters with such coatings. The antimicrobial coating minimizes the risk of microbe colonization on the outer surface of the catheter tubing when the catheter tubing is positioned within the vasculature of a patient.

In some embodiments, a catheter can be manufactured using a pre-treatment process which applies the antimicrobial coating to the catheter tubing prior to applying a lubricant over top of the coating. In such cases, the lubricant can function to retain the coating on the outer surface and also to limit the diffusion of the antimicrobial agent from the coating.

In some embodiments, a catheter can include an antimicrobial coating that does not block the visibility of flashback. Because the antimicrobial coating can be minimally transparent, the coating can be applied to the outer surface in a striped pattern or other pattern that leaves a portion of the outer surface uncoated or minimally coated. The flashback will then remain visible through the portions of the catheter tubing where no coating or minimal coating is present.

In one exemplary embodiment, the present invention is implemented as method for applying an antimicrobial coating on catheter tubing. A solution containing a solvent and an antimicrobial agent can be applied to a surface of catheter tubing. The solvent is then allowed to evaporate to leave behind a coating of the antimicrobial agent on the surface of the catheter tubing. A lubricant is then applied overtop the coating. The lubricant limits the rate of diffusion of the antimicrobial agent from the coating once the surface of the catheter tubing is subject to a fluid.

In some embodiments, the solvent has a vapor pressure that is at least equal to atmospheric pressure at a first temperature with the first temperature being the maximum safe temperature of the antimicrobial agent.

In some embodiments, the solvent comprises ethanol and the antimicrobial agent comprises chlorhexidine gluconate.

In some embodiments, the solvent causes the catheter tubing to expand to allow the antimicrobial agent to penetrate into the catheter tubing.

In another exemplary embodiment, the present invention is implemented as a method for applying an antimicrobial coating to catheter tubing in a pattern. An antimicrobial coating is applied over an outer surface of catheter tubing. The catheter tubing is then passed through a die to remove a portion of the antimicrobial coating from the outer surface such that a pattern of antimicrobial coating remains on the outer surface after the catheter tubing has passed through the die.

In some embodiments, the pattern comprises one or more stripes of antimicrobial coating.

In some embodiments, the outer surface of the catheter tubing comprises one or more channels and the pattern comprises the antimicrobial coating within the one or more channels.

In some embodiments, the pattern comprises one or more portions of the outer surface that do not include the antimicrobial coating or that include an insignificant amount of the antimicrobial coating so that contents of a lumen of the catheter tubing remain visible through the one or more portions.

In some embodiments, the pattern conforms to radiopaque material contained within the catheter tubing.

In some embodiments, the die includes one or more channels on an inner surface of the die. The one or more channels form the pattern.

In some embodiments, the catheter tubing comprises a segment of catheter tubing having a tip, and the antimicrobial coating is not applied to the tip.

In some embodiments, prior to applying the antimicrobial coating to the outer surface of the catheter tubing, a mandrel is inserted into one end of the catheter tubing to prevent the antimicrobial coating from entering the end. In some embodiments, this end comprises an end opposite a tip formed on the catheter tubing.

In another exemplary embodiment, the present invention is implemented as catheter tubing that comprises an outer surface having a circumference; and an antimicrobial coating applied to the outer surface in a pattern such that the pattern does not cover the entire circumference of the outer surface.

In some embodiments, the pattern comprises a plurality of stripes that are formed on the outer surface by passing the catheter tubing through a die after the antimicrobial coating is applied over the entire circumference of the outer surface.

In some embodiments, the plurality of stripes are formed within a plurality of channels in the outer surface.

In some embodiments, the catheter tubing further comprises strips of radiopaque material that extend along a length of the catheter tubing. The plurality of stripes of the pattern run substantially parallel with the strips of radiopaque material.

In some embodiments, the catheter tubing comprises a tip to which the antimicrobial coating does not extend.

Figure 1B:
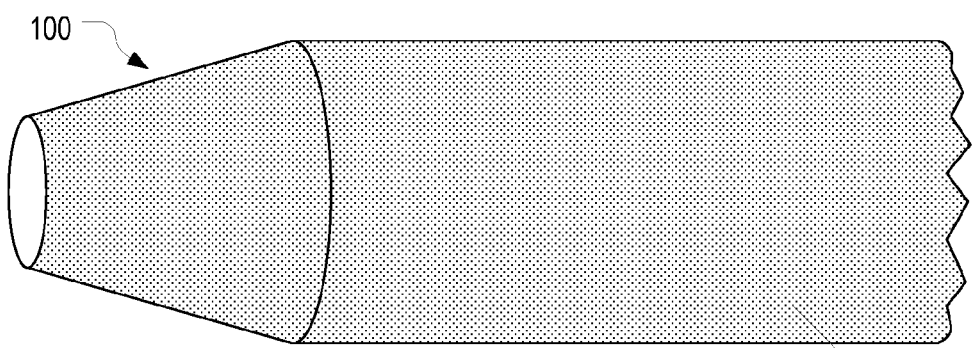
Figure 1C:
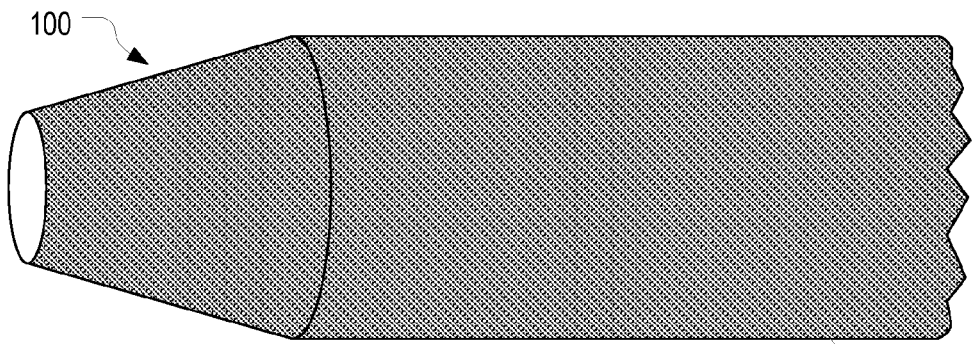

According to a first embodiment of the invention, a catheter tubing can be manufactured using a pretreatment process in which an antimicrobial coating is applied to the catheter tubing prior to applying a lubricant. A catheter tubing 100 manufactured using this pretreatment process is shown in FIGS. 1A-1C during various stages of manufacture. FIG. 1A illustrates catheter tubing 100 prior to the application of an antimicrobial coating. Catheter tubing 100 can be made of any material suitable for use intravenously as a catheter including polyurethane.

After passing through the pretreatment process, an antimicrobial coating 101 will be formed on the outer surfaces of catheter tubing 100 as is shown in FIG. 1B. Then, as shown in FIG. 1C, a lubricant 102 can be applied to catheter tubing overtop of antimicrobial coating 101. By applying lubricant 102 overtop of antimicrobial coating 101, the diffusion of antimicrobial agents within antimicrobial coating 101 can be limited to a desirable rate once catheter tubing 100 is positioned within the vasculature of a patient. In other words, the presence of lubricant 102 overtop of antimicrobial coating 101 slows the rate at which the antimicrobial agents dissolve from the coating into the bloodstream. This can minimize the possibility of toxicity due to an excess concentration of antimicrobial agents within the blood and also prolong the effective life of the coating.

FIGS. 2A-2D illustrate an example process for applying antimicrobial coating 101 and lubricant 102 to catheter tubing 100. In accordance with one or more embodiments of the invention, antimicrobial coating 101 can be applied to catheter tubing 100 using a process of applying a solution to the exterior surfaces of the catheter tubing and then letting a solvent within the solution evaporate to leave behind a coating containing antimicrobial agents.

Figure 2A:
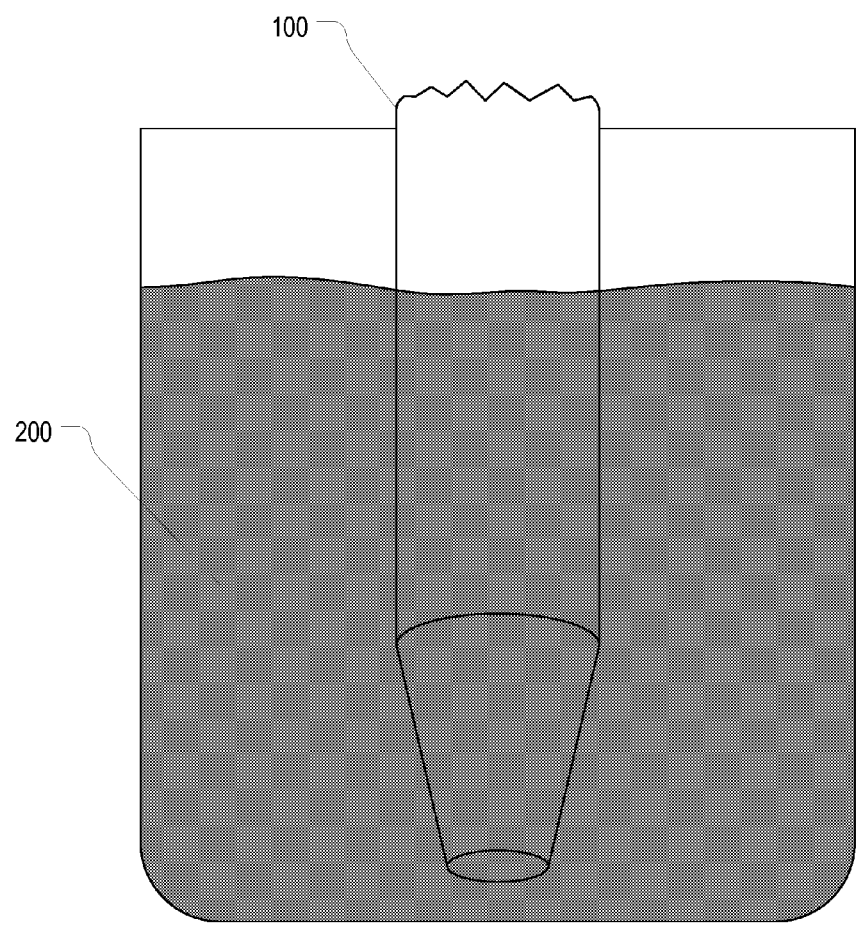
FIGS. 2A-2D illustrate a process of applying the antimicrobial coating 101 and lubricant 102 to catheter tubing 100 in accordance with one or more embodiments of the invention.

FIG. 2A illustrates catheter tubing 100 being dipped into a solution 200 that contains a solvent and an antimicrobial agent. FIG. 2A shows only a short portion of catheter tubing 100 being dipped; however, it is to be understood that substantial lengths of catheter tubing can be treated simultaneously in this manner. Further, although catheter tubing 100 is shown as already having a tip, in some embodiments, solution 200 can be applied to the catheter tubing prior to forming a tip or other feature on or within the catheter tubing. Also, in some embodiments, the end of catheter tubing 100 can be plugged to prevent solution 200 from entering the lumen of the tubing.

In some embodiments, the solvent and antimicrobial agent used in solution 200 can be chosen such that the vapor pressure of the solvent is approximately equal to or higher than atmospheric pressure at a temperature below the maximum safe temperature for the antimicrobial agent. In this way, an appropriate evaporation rate of the solvent can be obtained to ensure that the antimicrobial coating is appropriately formed. For example, solution 200 can comprise ethanol which has a vapor pressure of approximately 800 mmHg at 80° C. (which is near atmospheric pressure at 80° C.) and chlorhexidine gluconate (CHG) which can be safely used up to 90° C.

In some embodiments, by applying solution 200 to catheter tubing 100, the solvent can cause catheter tubing 100 to expand or swell. This expansion increases the porosity of the catheter tubing material (e.g. a polymer such as polyurethane) thereby allowing the antimicrobial agent to penetrate into the material. Once the solvent has evaporated from catheter tubing 100 and the material has returned to its normal size, an amount of the antimicrobial agent will remain within the material and can therefore provide antimicrobial properties beyond the life of a coating that is only on the surface of the tubing.

Figure 2B:
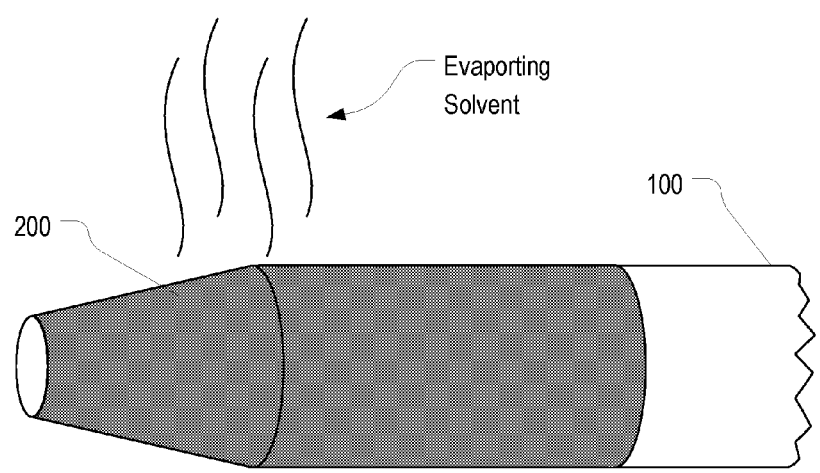
Figure 2C:
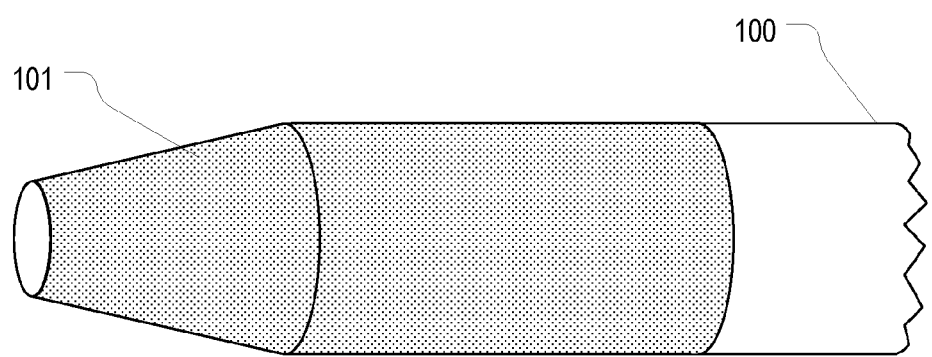

Returning to the figures, FIG. 2B illustrates catheter tubing 100 after it has been removed from solution 200. An amount of solution 200 remains on the surface of catheter tubing 100 from which the solvent evaporates. Evaporation may be accelerated by subjecting catheter tubing 100 to heat and/or reduced atmospheric pressure. As shown in FIG. 2C, after the solvent has fully evaporated, an antimicrobial coating 101 is left behind.

Figure 2D:
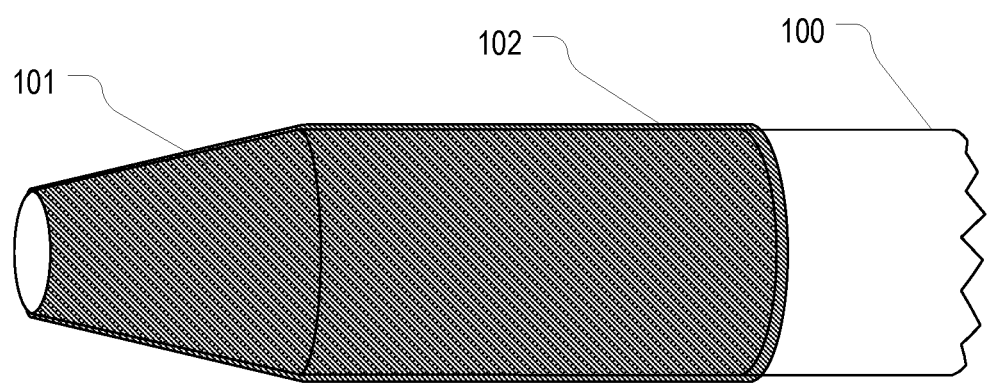

Finally, as shown in FIG. 2D, after antimicrobial coating 101 has been formed, a lubricant 102 can be applied (e.g. by spraying) overtop the coating. In addition to providing lubrication between catheter tubing 100 and a patient's skin, lubrication 102 can also act as a temporary sealant overtop of antimicrobial coating 101 to slow the rate at which the coating (or the antimicrobial agent within the coating) dissolves into a surrounding liquid such as blood.

In some embodiments, lubricant 102 can also contain an antimicrobial agent. In such cases, the antimicrobial agent within lubricant 102 can provide a microbial barrier at the insertion site of catheter tubing 100 where excess lubricant may pool upon insertion of the tubing. Suitable lubricants include those disclosed in U.S. Patent Publication No.: 2011/0065798 titled Anti-Infective Lubricant For Medical Devices And Methods For Preparing The Same, and U.S. Patent Publication No.: 2011/0009831 titled Antimicrobial Coating for Dermally Invasive Devices, each of which is incorporated herein by reference.

According to a second embodiment of the invention, an antimicrobial coating can be applied to a catheter tubing in a pattern. It may be desirable to apply a coating in a pattern (as opposed to a continuous layer covering the entire circumference of the tubing) for various reasons. For example, many coatings limit the visibility of flashback within the lumen of the catheter tubing. In such cases, the coating can be applied in a striped or other pattern that does not cover the entire circumference of the tubing thereby leaving portions of the catheter tubing free of the coating through which the flashback will remain easily visible. Also, continuous coatings are more prone to tear when the catheter tubing is hyper-stretched which is common during the manufacture of peripheral intravenous catheters. In such cases, a non-continuous coating can be used to minimize the possibility of tearing.

Figure 3A:
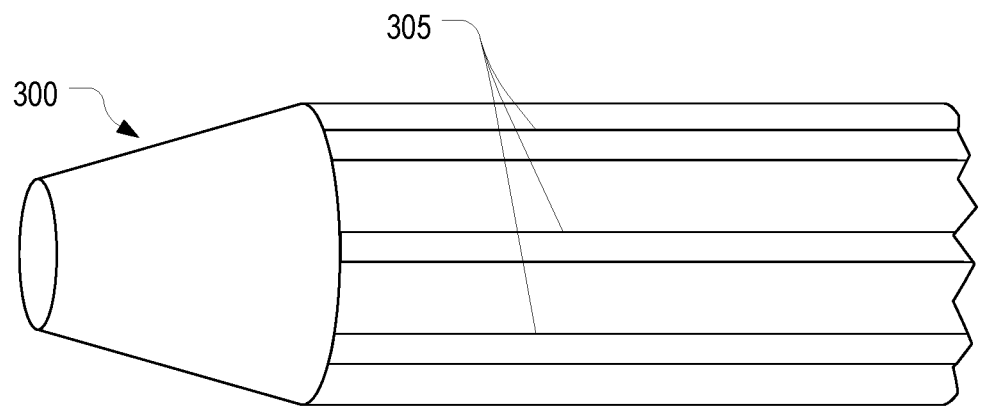
FIGS. 3A-3C illustrate a catheter tubing 300 that includes an antimicrobial coating 301 that is applied to the catheter tubing in a pattern that generally aligns with radiopaque material 305 contained within the catheter tubing.
Figure 3B:
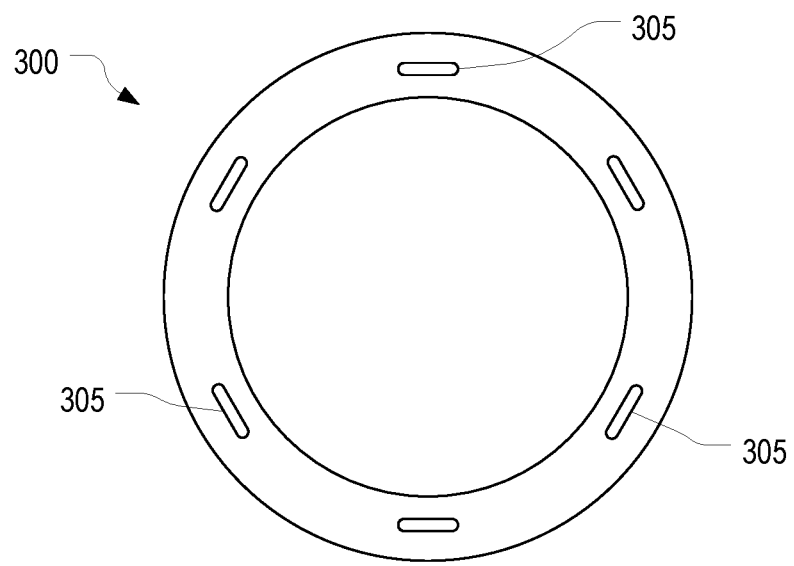
Figure 3C:
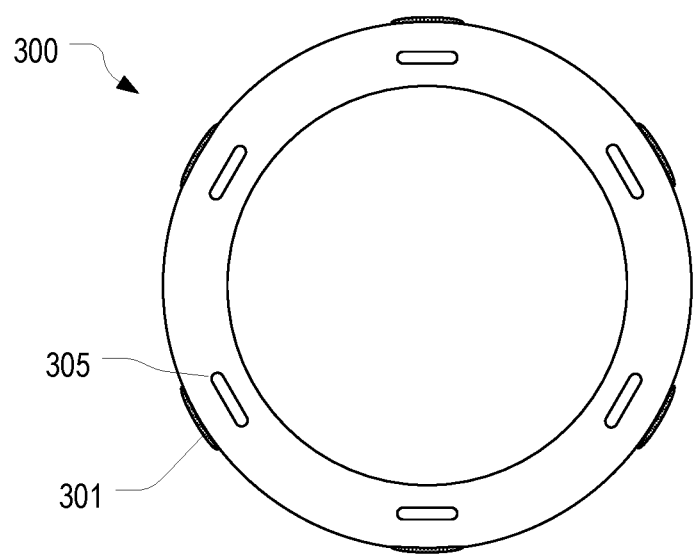

FIGS. 3A-3C illustrate one example embodiment of how an antimicrobial coating 301 can be applied to a catheter tubing 300 in a striped pattern. In this example, catheter tubing 300 includes radiopaque strips 305 as is shown in the perspective view of FIG. 3A and the cross-sectional view of FIG. 3B. Radiopaque strips 305 can be incorporated into catheter tubing 300 to enhance the visibility of catheter tubing 300 in an x-ray. To retain a portion of catheter tubing 300 through which flashback may be easily visible, antimicrobial coating 301 can be applied in a striping pattern that generally aligns with the radiopaque strips 305.

FIG. 3C illustrates how antimicrobial coating 301 can be applied on the outer surface of catheter tubing 300 in stripes. As shown, catheter tubing 300 includes six stripes of antimicrobial coating 301 that generally align with radiopaque strips 305. In this way, the portions of catheter tubing 300 between the radiopaque strips contain no or minimal antimicrobial coating 301 so as to not limit the visibility of flashback through these portions. Although the stripes of antimicrobial coating 301 are shown as being similar in width as the radiopaque strips 305, the stripes could have a greater or a lesser widths as desired.

Figure 4A:
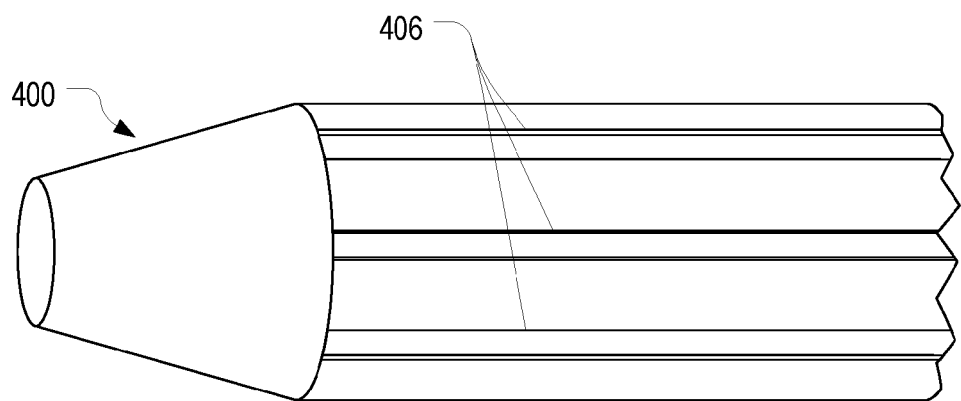
FIGS. 4A-4C illustrate a catheter tubing 400 that includes radiopaque material 405 and channels 406 for containing an antimicrobial coating 301.
Figure 4B:
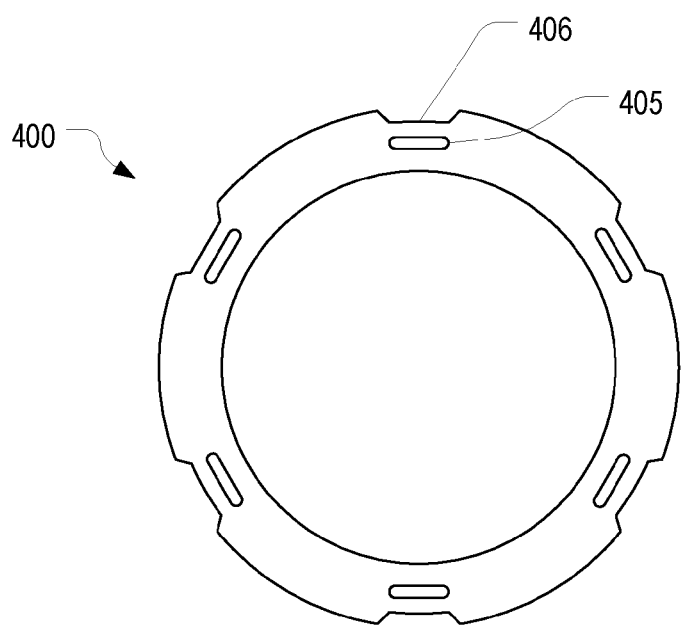
Figure 4C:
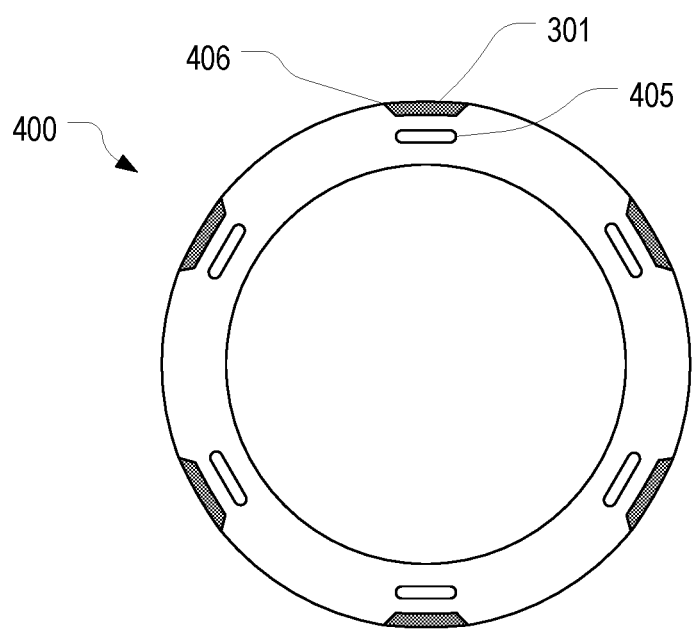

FIGS. 4A-4C illustrate another example embodiment of how an antimicrobial coating 301 can be applied to a catheter tubing 400 in a striped pattern. Catheter tubing 400 is similar to catheter tubing 300 except that catheter tubing 400 includes channels 406 that run generally parallel to radiopaque strips 405 as is best shown in the cross-sectional view of FIG. 4B. Antimicrobial coating 301 can be applied within these channels 406 while the portions of the outer surface of catheter tubing 400 remain free (or substantially free) of antimicrobial coating 301 to maintain the visibility of flashback through these portions.

In each of the embodiments depicted in FIGS. 3A-3C and 4A-4C, the antimicrobial coating 301 is not continuous around the entire circumference of the catheter tubing. Therefore, there is less likelihood that the antimicrobial coating will tear when the tubing is stretched. For example, even though these figures depict the catheter tubing as already having a tip, in some embodiments, the tip may be formed after the antimicrobial coating has been applied to the tubing. The non-continuous pattern of the coating will minimize the possibility that the coating will tear during tip formation, or during the process of securing the catheter to the catheter adapter, such as by swaging.

Also, in cases where the catheter tubing will be subject to a heat-forming process after the antimicrobial coating has been applied, the antimicrobial coating can consist of a thermoplastic adhesive matrix (e.g. polyurethane) which will allow the coating to deform with the catheter tubing during the heat-forming process. For example, oftentimes a tip is formed on the catheter tubing using a heat-forming process. In such cases, the antimicrobial coating can consist of a thermoplastic adhesive matrix to allow the antimicrobial coating to conform to the angled tip so that the tip retains the antimicrobial coating. Accordingly, even though FIGS. 3A and 4A imply that the antimicrobial coating may not be applied to the tip, the techniques of the present invention facilitate applying a pattern of antimicrobial coating that may extend along the body as well as along the tip of the catheter tubing whether the tip is formed before or after the application of the antimicrobial coating.

Figure 5A:
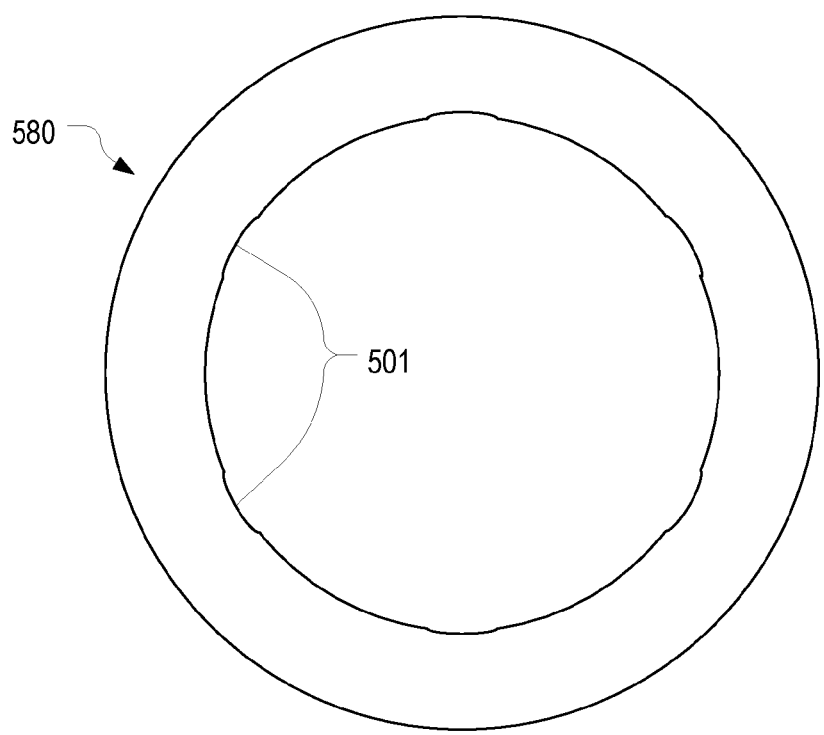
FIGS. 5A-5C illustrate how a die can be used to form a pattern of antimicrobial coating 301 on the exterior surfaces of a catheter tubing.
Figure 5B:
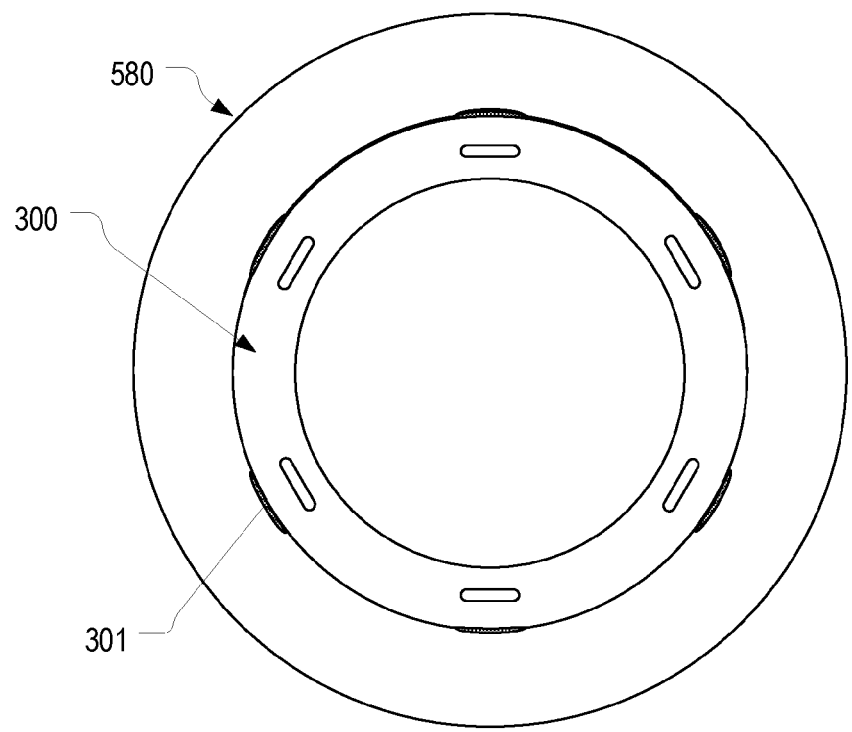
Figure 5C:
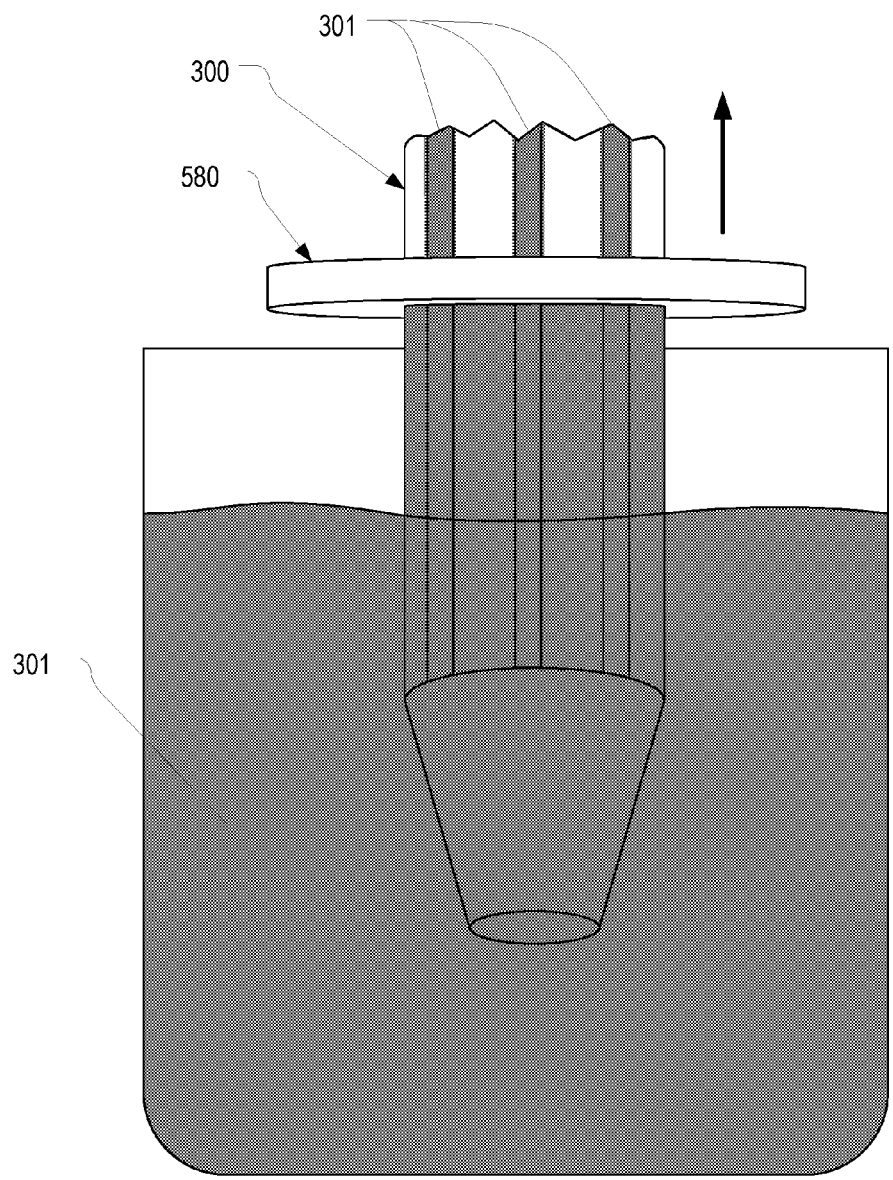

FIGS. 5A-5C illustrate an example process for applying an antimicrobial coating in a striped pattern. As shown in FIG. 5A, a die 580 can be used to apply the antimicrobial coating in a desired pattern. Die 580 includes a number of channels 501 that extends along its inner surfaces. As shown in FIG. 5B, channels 501 are configured to apply a pattern similar to the pattern shown in FIG. 3C (i.e. a pattern of six stripes that run generally parallel with the strips of radiopaque material).

FIG. 5C illustrates how a catheter tubing 300 can be passed through die 580 after antimicrobial coating 301 has been applied to the outer surfaces of the tubing. As shown, catheter tubing 300 is dipped into a solution containing antimicrobial coating 301. Then, as catheter tubing 300 is pulled out from the solution, the tubing is passed through die 580. The inner diameter of die 580 is configured to conform closely to the outer diameter of catheter tubing 300 so that die 580 wipes the antimicrobial coating from the outer surfaces of the tubing. However, because die 580 includes channels 501, six stripes of antimicrobial coating 301 will remain on the outer surface of catheter tubing 300. In some embodiments, after the antimicrobial coating has been applied to the catheter tubing, the coating can be cured (e.g. using heat or UV light).

Although FIG. 5C illustrates that catheter tubing 300 already includes a tip when the antimicrobial coating is applied, the tip could be formed after the coating is applied as described above. In such cases, by using a thermoplastic adhesive matrix, the antimicrobial coating can be reformed during a heat-forming process so that the stripes can conform to the angled surface of the tip. In this way, the antimicrobial stripes can extend along the full length of the catheter tubing.

In cases where the catheter tubing includes channels, a die without any channels (i.e. with a circular inner diameter) can be used to wipe the antimicrobial coating from all outer surfaces of the tubing thereby leaving the coating only within the channels. Also, dies having channels forming different patterns can also be used. For example, a die having more or fewer channels than die 580 or with channels of various widths or depths could be used. Also, a spiral pattern could be applied by rotating a die (or the catheter tubing) when the catheter tubing is passed through the die. Accordingly, the present invention extends to antimicrobial coating patterns of various types.

Although FIGS. 3A-3C, 4A-4C, and 5A-5C illustrate the application of a coating on a catheter tubing that includes radiopaque strips, the techniques for applying the coating in a pattern can equally be used on catheter tubing that does not include radiopaque material. For example, the same pattern could be applied to catheter tubing 300 and catheter tubing 400 even if they did not contain radiopaque strips 305 and 405 respectively.

The technique for applying a pattern using a die can typically be used on substantial lengths of catheter tubing. For example, a length of catheter tubing sufficient for making a number of catheters could be dipped in the solution containing antimicrobial agent 301 and then passed through die 580. Then, the catheter tubing can be cut into segments of a desired length and a tip can be formed on the segments. In such cases, it may be desirable to use an antimicrobial coating consisting of a thermoplastic adhesive matrix since it is common to form the tip using a heat-forming process.

However, in some cases, it is desirable to use an antimicrobial coating that consists of thermoset polymers which cannot be heat reformed. Because such coatings cannot be heat reformed, it is desirable to form segments having tips prior to applying the antimicrobial coating.

Figure 6A:
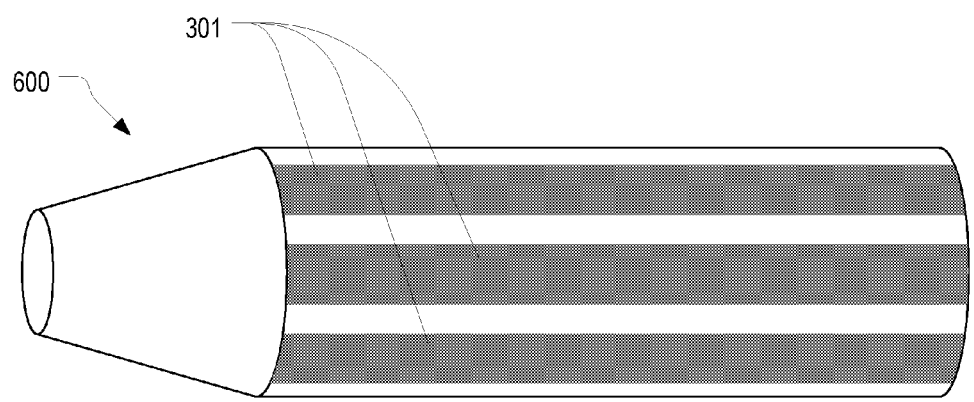
FIGS. 6A and 6B illustrate how an antimicrobial coating can be applied to a portion of catheter tubing.
Figure 6B:
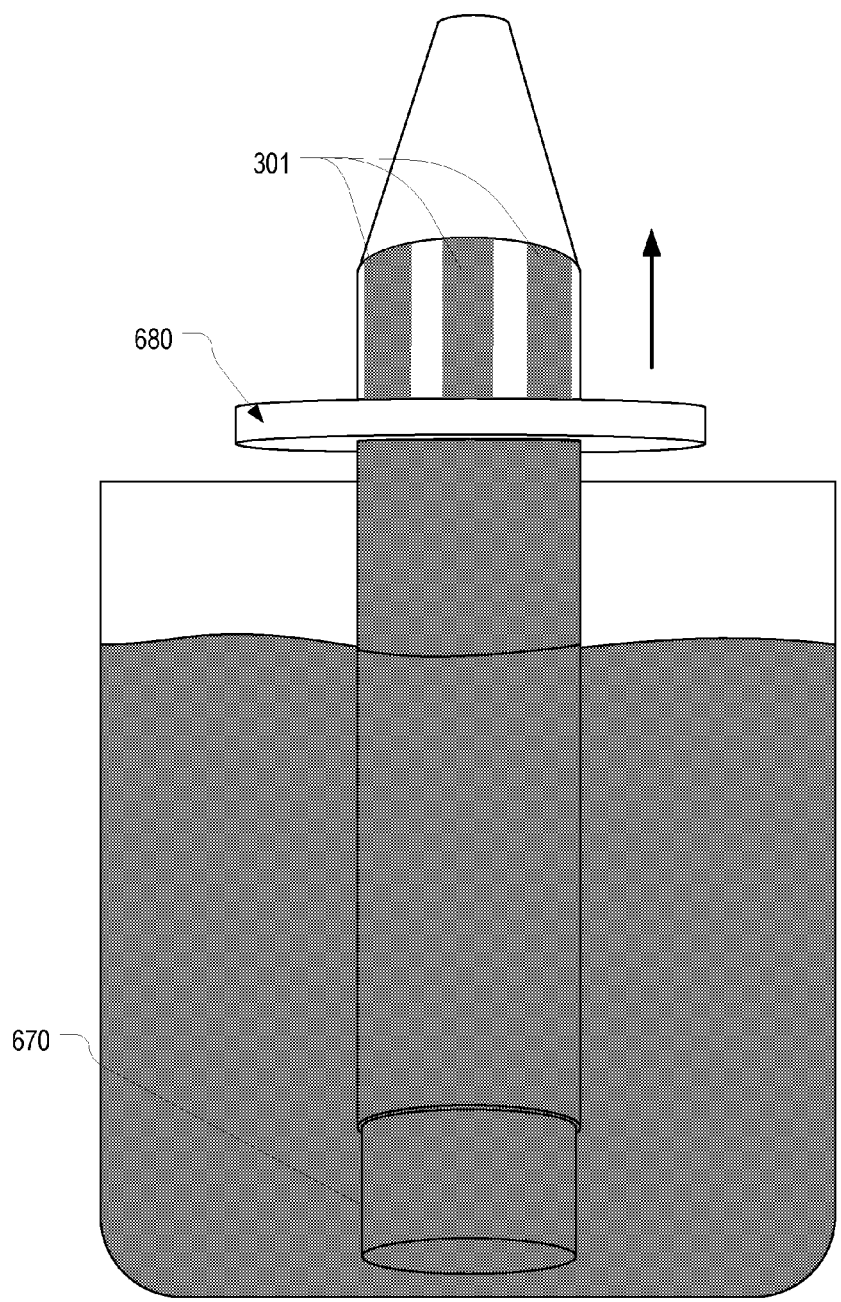

FIGS. 6A and 6B illustrate an example embodiment of how an antimicrobial coating can be applied to a segment of catheter tubing so that the coating does not extend along the tip as is shown in FIG. 6A. Because the above described processes involve dipping the catheter tubing into a solution containing the antimicrobial coating, an amount of the antimicrobial coating will enter into the lumen of the catheter tubing forming a coating on the inner surfaces of the tubing. This is not a problem when long lengths of catheter tubing are treated prior to cutting because the ends of the tubing can be cut off to remove any portion of the tubing having the coating on the inner surfaces. In contrast, when the catheter tubing is first cut into segments and tipped prior to receiving the antimicrobial coating, it is desirable to prevent the coating from entering into the lumen of the segments.

FIG. 6B illustrates how a pattern of antimicrobial coating can be applied to a segment of catheter tubing 600 using a similar process as shown in FIGS. 5A-5C while preventing the coating from entering inside the lumen of the segment and without applying the coating to the tip. As shown, prior to dipping the segment 600 in the solution containing the antimicrobial coating, a mandrel 670 is inserted into the end of segment 600 opposite the tip. The segment is then dipped mandrel end first into the solution while preventing the tip from being dipped. The segment can then be passed through die 680 to remove the excess antimicrobial coating and leave the desired pattern. The mandrel can then be removed.

In some embodiments, rather than removing the mandrel, the segment can be initially cut at a length that is slightly longer than necessary so that the portion of the segment containing the mandrel can be cut off. The resulting length of the segment after the mandrel is cut off can be the desired length for the catheter tubing.

In some embodiments, the formulations of antimicrobial coatings described in U.S. Patent Publication No.: 2010/0135949 titled Antimicrobial Coatings, which is incorporated by reference, can be used in the embodiments where a pattern is formed. In a specific example, such formulations can be applied to polyurethane catheter tubing and cured using UV light to form a chlorhexidine eluting layer that inhibits biofilm growth.

EXAMPLES

Example 1: Zone-of-Inhibition Test 20 gauge×1.25 inch catheters were pretreated to form an antimicrobial coating by dipping the catheters in a solution consisting of 5% CHG, 20% water, and 75% ethanol. The coated catheters were allowed to dry for two minutes. The coated catheters where then sprayed with a silicone lubricant emulsion containing 0.5% CHG w/w. Catheters that did not receive the pretreatment were also sprayed with the same lubricant emulsion. Small segments of both the pretreated and untreated catheters were then subjected to a zone-of-inhibition (ZOI) test. The pretreated catheters demonstrated up to 19 mm ZOI for *Staphylococcus epidermidis*, while the untreated catheters demonstrated only 1.5 mm ZOI.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. Catheter tubing comprising:
   an outer surface having a circumference;
   an antimicrobial coating applied to the outer surface in a pattern that does not cover an entirety of the outer surface, wherein the pattern includes a plurality of stripes spaced around the circumference and extending lengthwise along the outer surface; and
   a plurality of radiopaque strips disposed within the catheter tubing, wherein the radiopaque strips are aligned with and substantially parallel to the plurality of stripes.

2. The catheter tubing of claim 1, wherein the plurality of stripes are formed within a plurality of channels in the outer surface.

3. The catheter tubing of claim 1, wherein the catheter tubing comprises a tapered tip, wherein the plurality of stripes extend lengthwise along the outer surface to a portion of the outer surface proximate the tapered tip.

4. The catheter tubing of claim 1, further comprising a lubricant disposed over top of the antimicrobial coating.

5. Catheter tubing, comprising:

a tapered tip;

a body proximate the tapered tip, wherein the body includes an outer surface; and an antimicrobial coating applied to the outer surface in a pattern that does not cover an entirety of the outer surface, wherein the pattern includes a plurality of stripes spaced around a circumference of the body and extending lengthwise along the outer surface of the body to a portion of the outer surface proximate the tapered tip.

6. The catheter tubing of claim 5, further comprising a plurality of radiopaque strips disposed within the body, wherein the radiopaque strips are aligned with and substantially parallel to the plurality of stripes.

7. The catheter tubing of claim 5, wherein the plurality of stripes are formed within a plurality of channels in the outer surface.

8. The catheter tubing of claim 5, further comprising a lubricant disposed over top of the antimicrobial coating.

9. Catheter tubing comprising:

an outer surface having a circumference;

an antimicrobial coating applied to the outer surface in a pattern that does not cover an entirety of the outer surface, wherein the pattern includes a plurality of stripes spaced around the circumference and extending lengthwise along the outer surface; and a lubricant disposed on top of the antimicrobial coating.

10. The catheter tubing of claim 9, further comprising a tapered tip, wherein the plurality of stripes extend lengthwise along the outer surface to a portion of the outer surface proximate the tapered tip.

11. The catheter tubing of claim 9, further comprising a plurality of radiopaque strips disposed within the catheter tubing, wherein the radiopaque strips are aligned with and substantially parallel to the plurality of stripes.

12. The catheter tubing of claim 9, wherein the plurality of stripes are formed within a plurality of channels in the outer surface.

* * * * *